US010947583B2

(12) United States Patent
Shin et al.

(10) Patent No.: US 10,947,583 B2
(45) Date of Patent: Mar. 16, 2021

(54) GENE DETECTION DEVICE INCLUDING GOLD NANOPARTICLES AND GENE DETECTION METHOD USING GOLD NANOPARTICLES

(71) Applicant: Korea University Research and Business Foundation, Seoul (KR)

(72) Inventors: Sehyun Shin, Seoul (KR); Wonhwi Na, Seoul (KR); Daeho Jang, Ansan-Si (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 15/819,979

(22) Filed: Nov. 21, 2017

(65) Prior Publication Data

US 2018/0155769 A1      Jun. 7, 2018

(30) Foreign Application Priority Data

Nov. 21, 2016   (KR) .......................... 10-2016-0155143

(51) Int. Cl.
| | | |
|---|---|---|
| *C12Q 1/68* | (2018.01) | |
| *C12Q 1/6825* | (2018.01) | |
| *C12Q 1/6834* | (2018.01) | |
| *C12N 9/22* | (2006.01) | |
| *C12Q 1/686* | (2018.01) | |
| *C12Q 1/6827* | (2018.01) | |

(52) U.S. Cl.
CPC ............ *C12Q 1/6825* (2013.01); *C12N 9/22* (2013.01); *C12Q 1/686* (2013.01); *C12Q 1/6827* (2013.01); *C12Q 1/6834* (2013.01); *C12Q 2563/137* (2013.01); *C12Q 2563/155* (2013.01)

(58) Field of Classification Search
CPC ............... C12Q 1/6823; C12Q 1/6825; C12Q 2521/319; C12Q 2565/632
See application file for complete search history.

(56) References Cited

U.S. PATENT DOCUMENTS

| | | | | |
|---|---|---|---|---|
| 5,403,711 A | * | 4/1995 | Walder ................. | C12Q 1/6876 435/6.1 |
| 2008/0292545 A1 | * | 11/2008 | Lin ....................... | G01N 33/585 424/1.29 |
| 2009/0280188 A1 | * | 11/2009 | Mirkin ................. | C12Q 1/6834 424/499 |
| 2012/0058471 A1 | * | 3/2012 | Graham ............... | C12Q 1/6823 435/6.11 |

(Continued)

OTHER PUBLICATIONS

Fan et al "Exonucleas III-based and gold nanoparticle-assisted DNA detection with dual singla annplificaiton" Biosensors and Bioelectroinics, 2012, 33: 211-215. (Year: 2012).*

(Continued)

*Primary Examiner* — Betty J Forman
(74) *Attorney, Agent, or Firm* — Fox Rothschild LLP (57) ABSTRACT

Disclosed are a gene detection device including gold nanoparticles and a gene detection method using gold nanoparticles. The use of the gene detection device and the gene detection method avoids the need for special equipment, such as a thermal cycler, which is essential for 3-stage heating in conventional PCR-based gene amplification techniques. In addition, the gene detection device and the gene detection method enable rapid and sensitive quantitative analysis and multiple detection.

4 Claims, 7 Drawing Sheets

(56) References Cited

U.S. PATENT DOCUMENTS

2013/0085078 A1* 4/2013 Schrader .............. C12Q 1/6818
506/9

OTHER PUBLICATIONS

Zuo et al., "Sensitive and Selective Amplified FLuorescence DNA Detection Based on Exonuclease III-Aided Target Recycling," J. Am. Chem. Soc. (2010); 132:1816-1818.
He et al., "Colloidal Au-Enhanced Surface Plasmon Resonance for Ultrasensitive Detection of DNA Hybridization," J. Am. Chem. Soc. (2000); 122:9071-9077.

* cited by examiner

GENE DETECTION DEVICE INCLUDING GOLD NANOPARTICLES AND GENE DETECTION METHOD USING GOLD NANOPARTICLES

BACKGROUND OF THE INVENTION

1. Field of the Invention

The present invention relates to a gene detection device including gold nanoparticles and a gene detection method using gold nanoparticles.

2. Description of the Related Art

Diagnostic methods for diseases using genes have been widely utilized. However, research has continued on methods for genetic diagnosis in which an extremely small number of target genes in samples are amplified for observation.

Polymerase chain reaction (PCR) techniques have been used to amplify genes. According to a traditional PCR technique, PCR is performed by adding reagents, such as a polymerase and primers, to a sample, 30-40 cycles of temperature variation proceed using a thermal cycler, and an investigation is made as to whether a target gene is present in a final product. However, a long time is taken to control the temperatures in the individual steps due to the high heat capacity of a heating block of the thermal cycler. For example, 2-2.5 hours are required except the time to prepare for measurement. Furthermore, traditional PCR techniques are limited to qualitative analysis rather than quantitative analysis.

Thus, real-time PCR was developed in which a gene in a sample is amplified, a reagent designed to emit fluorescence in the amplified gene is used, and the intensity of fluorescence is measured every time each cycle ends so that the initial amount of the gene in the sample is estimated from the time it takes for the amplification to take place. However, the very high price of the reagent designed to emit fluorescence leads to an increase in diagnostic cost. Further, the use of a heating block with high heat capacity in real-time PCR as in traditional PCR requires a long time for temperature control, resulting in a long measurement time.

Since existing PCR techniques are based on the amplification of target genes, an error arising at the initial stage of the reaction is also continuously amplified, which increases the possibility of false results. Furthermore, genetic diagnostic methods for diseases, such as cancer, necessitate the detection of genetic mutations, including point mutations or deletion mutations, in the entire base sequences. This necessity limits the use of existing PCR-based techniques for genetic diagnosis.

Recent molecular diagnostic methods employ next generation sequencing (NGS) techniques for direct analysis of genetic mutations in DNA sequences but have the disadvantages that the procedure is complicated and only a limited number of samples can be measured at one time (Elaine R. Mardis, *Trends in Genetics*, 24(3): 133-141, 2008).

Under these circumstances, there is an urgent need for a method that enables the detection of small numbers of multiple target genes in a sample and particularly the detection of mutated gene sequences, for example, for cancer diagnosis, thus being suitable for various applications, such as disease diagnosis.

As a result of an effort to develop a method for the detection of small numbers of multiple target genes, the present inventors have found that the use of gold nanoparticles enables the detection of mutated gene sequence and rapid and sensitive quantitative analysis and yields a number of products from one target gene, enabling multiple detection. The present invention has been accomplished based on this finding.

SUMMARY OF THE INVENTION

One object of the present invention is to provide a gene detection device including gold nanoparticle. A further object of the present invention is to provide a gene detection method using gold nanoparticles.

One aspect of the present invention provides a gene detection device including: gold nanoparticles; probe DNAs, each of which is composed of a target capture DNA having a base sequence complementary to and binding to a target gene and a sensing DNA having a base sequence so as to bind to the surface of a sensor, attached to the gold nanoparticles and whose end is functionalized so as to bind to the gold nanoparticles; probe linker DNAs having a base sequence complementary to and binding to the sensing DNAs; a deoxyribonuclease (DNase) cleaving double strands from the 3' ends of the target capture DNAs of the probe DNAs double-stranded with the target gene; and a sensor immobilized with the probe linker DNAs to detect the target gene.

A further aspect of the present invention provides a gene detection method including: (a) attaching a controlled number of probe DNAs for target gene detection to the surface of gold nanoparticles to form probe-gold nanoparticles; (b) mixing the probe-gold nanoparticles in a sample such that distal target capture DNAs of the probe DNAs are hybridized with a target gene; (c) degrading the exposed 3' ends of the target capture DNAs complementarily bound to the target gene by a nuclease to remove the complementarily bound DNAs and target gene; (d) forming products in which non-complementary sensing DNAs of the probe DNAs remain in the probe-gold nanoparticles and complementarily bind to the surface of a sensor; (e) repeating (b) to (d) to obtain a large number of the products; and (f) allowing the products to complementarily bind to probe linker DNAs immobilized on the sensor surface to generate detection signals.

The use of the gene detection device and the gene detection method according to the present invention avoids the need for special equipment, such as a thermal cycler, which is essential for 3-stage heating in conventional PCR-based gene amplification techniques. In addition, the gene detection device and the gene detection method of the present invention enable rapid and sensitive quantitative analysis and multiple detection of mutations, including genetic mutations.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Unless defined otherwise, all technical and scientific terms used herein have the same meaning as commonly understood by the ordinary skilled in the art expert. In general, the experimental method described in the nomenclature used herein and in the following is well-known and commonly used in the art.

Figure 1:
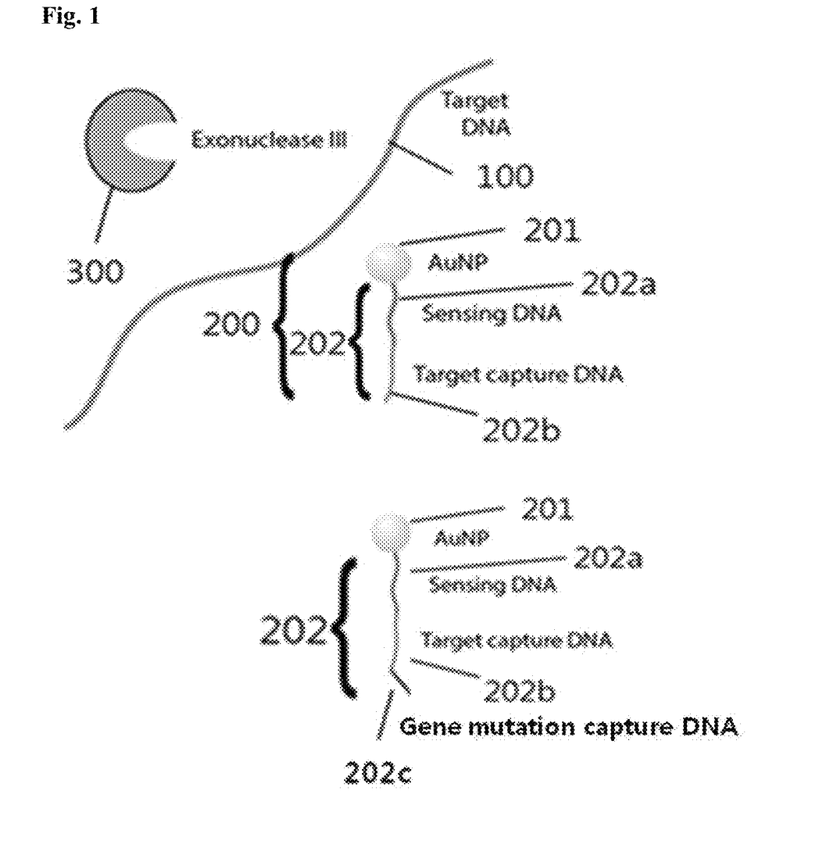
FIG. 1 shows materials for the detection of a target gene using probe DNA-immobilized gold nanoparticles. A target gene, a probe DNA-immobilized gold nanoparticle, a gold nanoparticle, a probe DNA, a sensing DNA, a target capture DNA, a gene mutation capture DNA, and a DNase are denoted by 100, 200, 201, 202, 202a, 202b, 202c, and 300, respectively.
Figure 3:
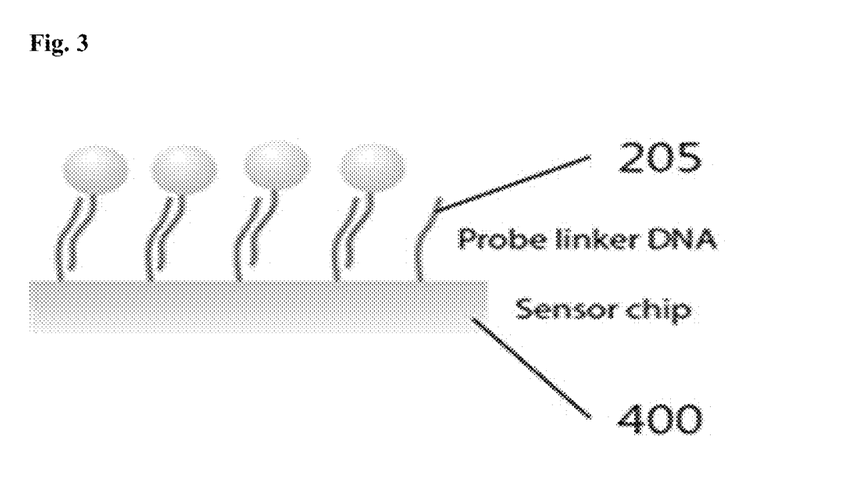
FIG. 3 shows a process for the detection of products. Probe linker DNAs 205 are immobilized on the surface of a sensor 400.

In one aspect, the present invention is directed to a gene detection device including: gold nanoparticles 201; probe DNAs 202, each of which is composed of a target capture DNA 202b having a base sequence complementary to and binding to a target gene and a sensing DNA 202a having a base sequence so as to bind to the surface of a sensor, attached to the gold nanoparticles and whose end is functionalized so as to bind to the gold nanoparticles; probe linker DNAs 205 having a base sequence complementary to and binding to the sensing DNAs; a deoxyribonuclease (DNase) 300 cleaving double strands from the 3' ends of the target capture DNAs of the probe DNAs double-stranded with the target gene; and a sensor 400 immobilized with the probe linker DNAs to detect the target gene (see FIGS. 1 and 3).

In the present invention, each of the probe DNAs may further include a gene mutation capture DNA bound to the 3' end of the target capture DNA (FIG. 1). The gene mutation capture DNA is 4-mer in length and its first base sequence attached to the target capture DNA is complementary to and binds to the mutated gene.

In the present invention, the genetic mutation may be a point mutation or a deletion mutation.

In the present invention, the gold nanoparticles amplify detection signals based on their mass enhancement effect or nanoplasmonic phenomenon.

In the present invention, the sensor is designed to measure surface characteristics, including changes in mass, electrical properties, and refractive index, but is not limited thereto.

In the present invention, the gold nanoparticles may be replaced by other types of nanoparticles that have physical properties adapted to amplify detection signals depending on the type of the sensor.

In the present invention, the gene detection device may further include spacers.

In the present invention, the gene detection device is capable of detecting multiple target genes.

In a further aspect, the present invention is directed to a gene detection method including: (a) attaching a controlled number of probe DNAs for target gene detection to the surface of gold nanoparticles to form probe-gold nanoparticles; (b) mixing the probe-gold nanoparticles in a sample such that distal target capture DNAs of the probe DNAs are hybridized with a target gene; (c) degrading the exposed 3' ends of the target capture DNAs complementarily bound to the target gene by a nuclease to remove the complementarily bound DNAs and target gene; (d) forming products in which non-complementary sensing DNAs of the probe DNAs remain in the probe-gold nanoparticles and complementarily bind to the surface of a sensor; (e) repeating (b) to (d) to obtain a large number of the products; and (f) allowing the products to complementarily bind to probe linker DNAs immobilized on the sensor surface to generate detection signals.

In the present invention, the sensor is one designed for surface measurement but is not limited thereto.

In the present invention, the gold nanoparticles may be replaced by other types of nanoparticles, such as polymer particles, magnetic particles, metallic particles, and fluorescent particles, that have physical properties adapted to amplify detection signals depending on the type of the sensor.

In the present invention, short DNAs or surface treating materials whose length is smaller than the probe DNAs may be added as spacers to prevent the probe DNAs from adhering to the entire surface of the gold nanoparticles and to allow only a predetermined number of the probe DNAs to be attached to the surface of the gold nanoparticles. The surface treating materials may be, for example, polyethylene glycol (PEG) or 11-mercapto-1-undecanol molecules.

In the present invention, the DNase floats freely in the sample by diffusion, digests the double-stranded target gene and the target capture DNAs of the gold nanoparticles immobilized with the probe DNAs and this procedure is repeated to form a number of products from one target gene, achieving a better signal amplification effect from the increased number of products.

In order to prevent the generation of false-positive signals when the gold nanoparticles attached with the probe DNAs do not react with the target gene and are detected on the sensor surface, the method may further include using short DNA strands as primers complementarily binding to the target capture DNAs, a polymerase synthesizing complementary blocking DNAs along the probe DNAs starting from the primers bound to the target capture DNAs, and dNTPs and a DNA polymerase as materials for the blocking DNAs such that the probe DNAs attached to the unreacted gold nanoparticles are made double-stranded.

In the present invention, when the target gene is provided in plurality, the target capture DNAs of the probe DNAs may have different base sequences and bind to corresponding genes only and the sensing DNAs may have different base sequences and form double strands with different probe linker DNAs on the sensor surface, enabling multiple detection.

In the present invention, the DNase does not degrade the 3' end of DNA having a 4-mer or longer overhang. The overhang may be a single-stranded DNA fragment.

As described earlier, each of the probe DNAs may further include a gene mutation capture DNA bound to the 3' end of the target capture DNA (FIG. 1). The gene mutation capture DNA is 4-mer in length and its first base sequence attached to the target capture DNA is complementary to and binds to the mutated gene.

Figure 9:
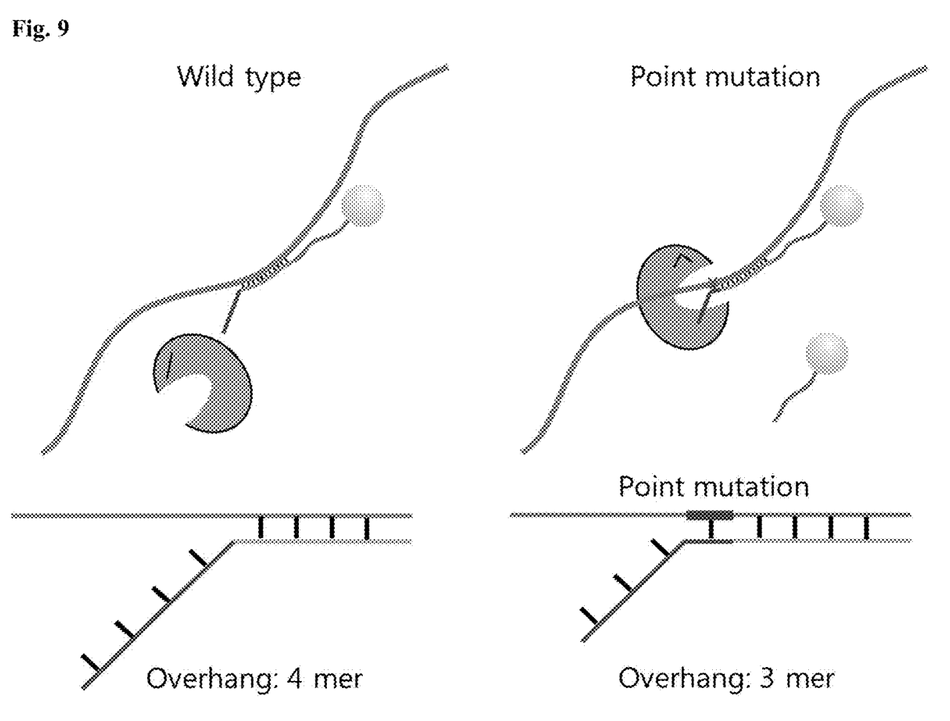
FIG. 9 shows a principle for the detection of a point mutation as a genetic mutation. Specifically, based on the feature that DNase cannot degrade a 4-mer or longer single-stranded overhang, the first base sequence of a point mutation capture DNA having a base sequence complementary to a target gene having a point mutation, that is, 1-mer of the 4-mer point mutation capture DNA, binds to the target gene, and the remaining 3-mer is degraded by a DNase to form a reaction product 200a, whereas 1-mer of the 4-mer point mutation capture DNA does not bind to a target gene without a point mutation, and as a result, the 4-mer overhang remains intact without being degraded by a DNase, failing to form a reaction product.

Due to these features, when the first base sequence of the gene mutation capture DNA complementarily binds to the mutated gene, the length of the gene mutation capture DNAs is reduced 3-mer (i.e. a 3-mer overhang remains) and the gene mutation capture DNA is degraded by the DNase to form a reaction product 200a. In contrast, when the first base sequence of the gene mutation capture DNA does not bind to a non-mutated normal gene, the 4-mer gene mutation capture DNA is maintained (i.e. a 4-mer overhang remains intact) and the gene mutation capture DNA is not degraded by the DNase, failing to form a reaction product. That is, the use of the gene mutation capture DNAs attached to the ends of the target capture DNAs allows the DNase to act on a mutated gene and prevents the DNase from acting on a normal gene. In conclusion, the formation of reaction products only in the presence of a mutated gene enables the detection of the mutated gene (FIG. 9).

EXAMPLES

The present invention will be explained in more detail with reference to the following examples. It will be appreciated by those skilled in the art that these examples are merely illustrative and the scope of the present invention is not construed as being limited to the examples. Thus, the true scope of the present invention should be defined by the appended claims and their equivalents.

Example 1: Detection of Target Gene Using Gold Nanoparticles

A controlled number of probe DNAs for target gene detection were attached to the surface of gold nanoparticles to form probe-gold nanoparticles. The probe-gold nanoparticles were mixed in a subject sample such that distal target capture DNAs of the probe DNAs were hybridized with a target gene. The target capture DNAs were designed to have a complementary sequence so as to bind to a specific sequence of the target gene. Then, the exposed 3' ends of the target capture DNAs complementarily bound to the target gene were degraded by a nuclease to remove the complementarily bound DNAs and target gene. As a result, products were obtained in which non-complementary sensing DNAs of the probe DNAs of the probe-gold nanoparticles remained in the probe-gold nanoparticles and were complementarily bound to the surface of a sensor.

When the above procedure was repeated, a large number of the products could be obtained from a small amount of the target gene because the target gene was degraded by the nuclease.

The large number of the products were complementarily bound to linker DNAs, which had previously been immobilized on the sensor surface, to generate detection signals.

1-1: Preparation of Materials for Target Gene Detection Using Gold Nanoparticles A single-stranded gene was used as a target gene. A double-stranded gene was denatured into a single strand by heating to 95° C. before use as a target gene. RNA was converted into cDNA by reverse transcription and the cDNA was denatured into a single-stranded gene as a target gene.

For gene detection, probe DNAs were immobilized on gold nanoparticles. Before the immobilization of the probe DNAs, the 5' ends of the probe DNAs were functionalized with thiol groups, through which the probe DNAs were bound to the gold surface. Alternatively, the surface of the gold nanoparticles was functionalized biotin and immobilized with streptavidin, and then the 5' ends of the probe DNAs were functionalized with biotin, through which the probe DNAs were bound to the gold nanoparticles.

Each of the probe DNAs was composed of a sensing DNA binding to the surface of a sensor chip and a target capture DNA connected to the sensing DNA.

Exonuclease III as a DNase was used to digest the 3' ends of the double-stranded DNAs. In the case where any type of DNase or RNase is used instead of exonuclease III, the probe DNAs are structurally modified before use.

1-2: Formation of Products Generating Detection Signals

The gold nanoparticles immobilized with the probe DNAs were hybridized with the target gene to form double strands. Only the target capture DNAs complementary to the base sequence of the target gene were hybridized with the target gene to form double strands (1 in FIG. 2).

The double-stranded target capture DNAs were degraded one by one into dNTPs from the 3' ends thereof. The single-stranded 3' end of the target gene was not degraded by the DNase because (2 in FIG. 2).

Detected products 200a were formed in which only the non-complementary sensing DNAs of the probe DNAs remained because the double-stranded target capture DNAs were completely degraded by the DNase. The target gene returned to its original single strand form without damage (3 in FIG. 2).

Figure 2:
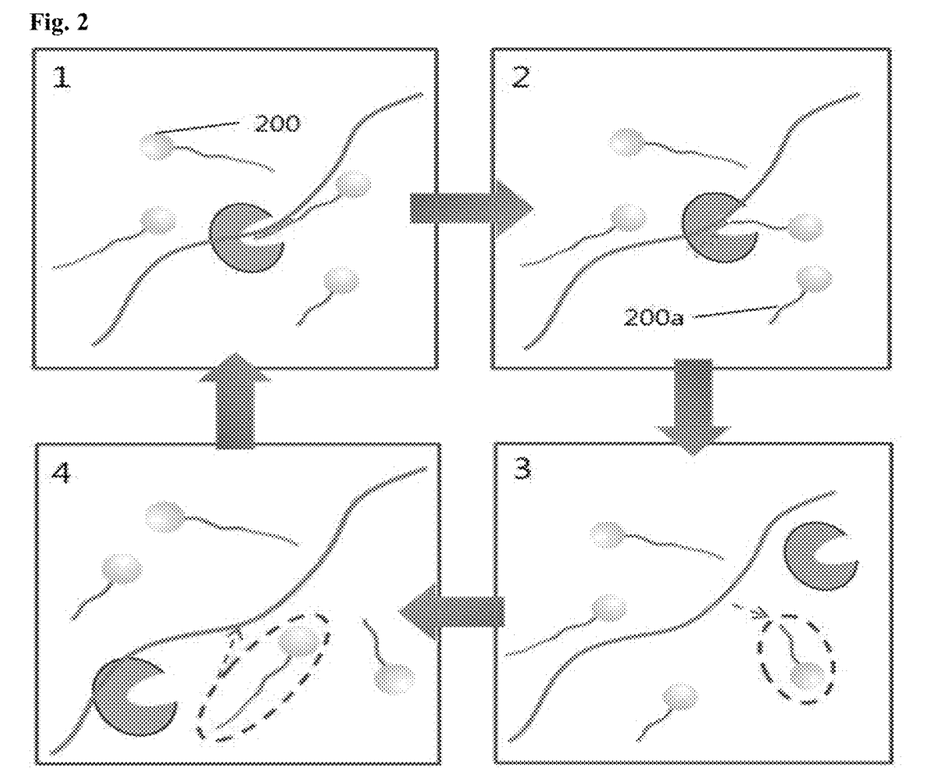
FIG. 2 shows a procedure for forming detection signal-generating products using probe DNA-immobilized gold nanoparticles to detect a target gene. 1 shows a process for double-strand hybridization of probe DNA-immobilized gold nanoparticles 200 with a target gene, 2 shows a process in which a DNase degrades double-stranded target capture DNAs one by one into dNTPs from the 3' ends of the target capture DNAs, 3 shows a process for forming detected products 200a in which the double-stranded target capture DNAs are completely degraded, leaving only non-complementary sensing DNAs of the probe DNAs, and 4 shows a process in which unreacted probe DNA-immobilized gold nanoparticles present in the sample form double strands with the target gene.

The unreacted gold nanoparticles immobilized with the probe DNAs present in the reaction sample formed double strands with the target gene (4 in FIG. 2).

This procedure proceeded by the target gene, the gold nanoparticles immobilized with the probe DNAs, and the DNase floating freely in the reaction sample by diffusion without any external energy supply. As the procedure was repeated, a large number of the detected products could be obtained from one target gene. Therefore, a better signal amplification effect could be achieved by the formation of a larger number of the detected products than the target gene.

After the procedure was repeated, the sample was exposed to a temperature of −70° C. for 15 min to inactivate the DNase.

1-3: Detection of the Products

Probe linker DNAs 205 are immobilized on the sensor surface. The probe linker DNAs had a base sequence complementary to the sensing DNAs so as to bind to the sensing DNAs. Thus, the detected products formed in Example 1-2 were capable of specific binding to the sensor surface. The sensor refers to one that can operate in various surface detection modes and brings about an enhancement in detection signal by the larger mass of the gold nanoparticles than that of the target gene. Particularly, when the sensor is a surface plasmon resonance sensor, a nanoplasmonic phenomenon induced by the gold nanoparticles produces a synergistic effect with the surface plasmon phenomenon of the sensor chip surface to obtain stronger detection signals, contributing to a better detection signal amplification effect (FIG. 3).

1-4: Removal of Signals Generated from the Gold Nanoparticles

False-positive signals from the gold nanoparticles that remained unreacted due to the absence of the target gene in the sample or the probe DNA-immobilized gold nanoparticles that were not converted into products, were removed.

Figure 4:
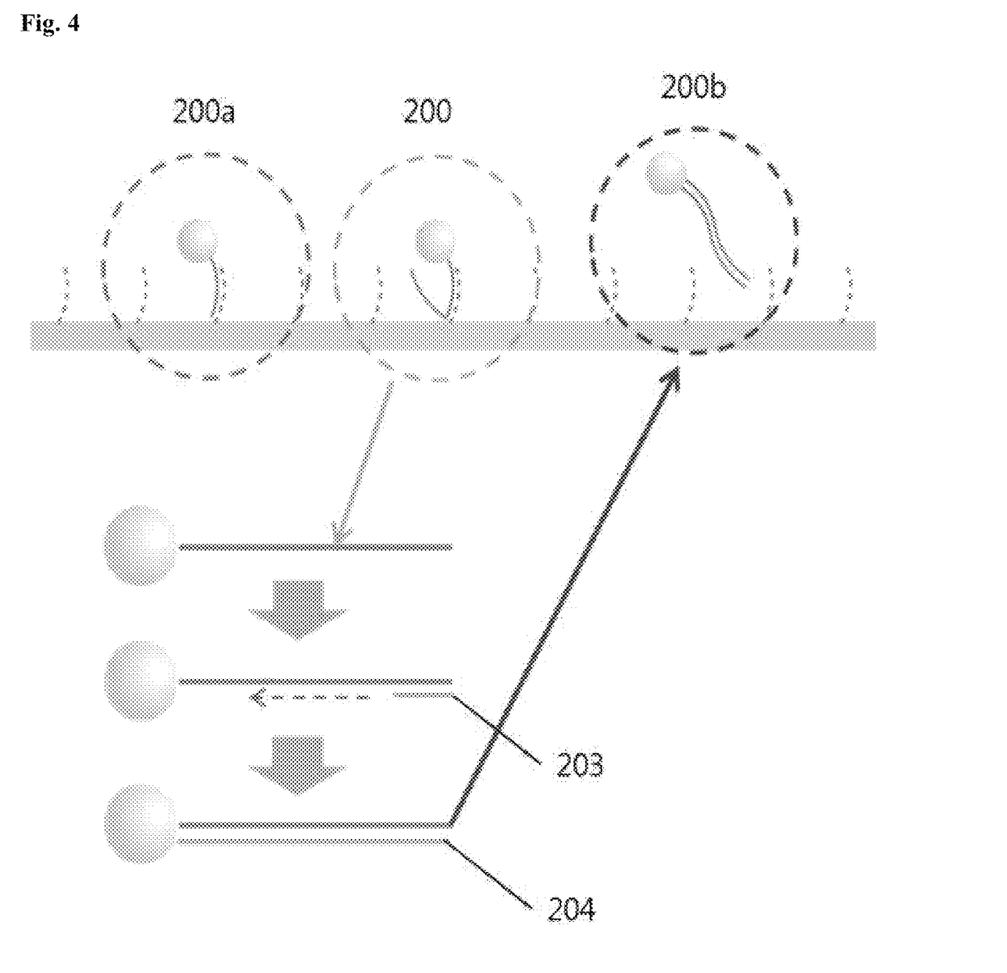
FIG. 4 shows a process for the removal of false-positive signals from a gold nanoparticle that remains unreacted due to the absence of a target gene in a sample and a probe DNA-immobilized gold nanoparticle that is not converted into a product. A probe DNA-immobilized gold nanoparticle, a gold nanoparticle attached with a sensing DNA without a target capture DNA, a blocked gold nanoparticle, a primer specifically binding to a target capture DNA, and a blocking DNA are denoted by 200, 200a, 200b, 203, and 204, respectively.

The distal target capture DNAs of the probe DNAs were not found in the detected products. Accordingly, the detected products were easily capable of complementary binding to the probe linker DNAs immobilized on the sensor surface but the unreacted gold nanoparticles 200 were hindered by the remaining target capture DNAs, which explains their low binding force. In contrast, the flexible single-stranded gene needs to be blocked to completely prevent complementary binding with the sensing DNAs. The blocking process was carried out in such a manner that PCR reagents including primers 203, a DNA polymerase, and dNTPs were added, followed by exposure to an annealing temperature of ~50° C. to allow the primers to complementarily bind to the target capture DNAs. The primers were specifically bound to the distal target capture DNAs of the unreacted gold nanoparticles immobilized with the probe DNAs. The annealing temperature varied depending on the base sequence of the primers. Thereafter, a DNA polymerization process proceeded by exposure to an extension temperature of ~75° C. to form blocking DNAs 204, which formed complementary double strands with the probe DNAs of the unreacted gold nanoparticles. The sensing DNAs of the gold nanoparticles 200*b* having undergone the blocking process were not exposed in the form of single strands and were thus not bound to the probe linker DNAs on the sensor surface (FIG. 4).

Figure 5:
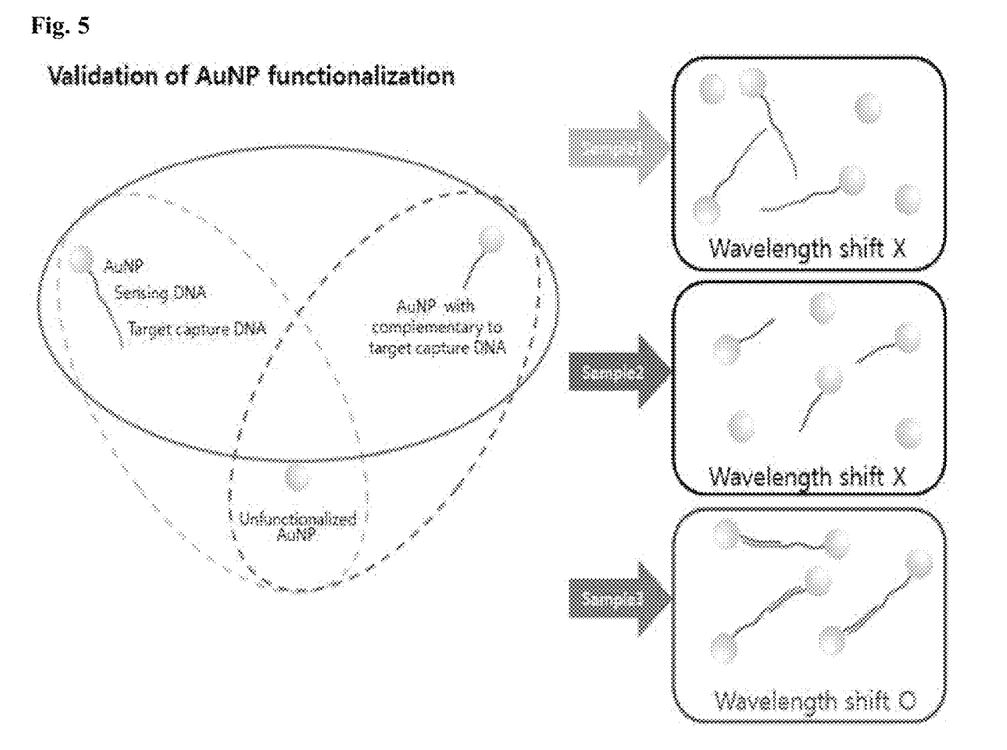
FIG. 5 shows an experimental method for validating the surface treatment of gold nanoparticles in Example 2-1.

Example 2: Validation Experiments 2-1: Validation of Surface Treatment of the Gold Nanoparticles An experiment was conducted to investigate whether the probe DNAs were normally bound to the surface of the gold nanoparticles. The gold nanoparticles (shown at the top left of FIG. 5), the gold nanoparticles attached with the sensing DNAs having a base sequence complementary to and binding to the target capture DNAs of the gold nanoparticles (shown at the top right of FIG. 5), and the gold nanoparticles simply treated to prevent them from aggregating (shown at the bottom of FIG. 5) were mixed in pairs. Sample 1 was a mixture of the gold nanoparticles shown at the top left of FIG. 5 and the gold nanoparticles shown at the bottom of FIG. 5, Sample 2 was a mixture of the gold nanoparticles shown at the top right of FIG. 5 and the gold nanoparticles shown at the bottom of FIG. 5, Sample 3 was a mixture of the gold nanoparticles shown at the top left of FIG. 5 and the gold nanoparticles shown at the top right of FIG. 5. In Sample 1 and Sample 2, no binding between the different types of gold nanoparticles was observed. In Sample 3, the complementary gold nanoparticles were bound in pairs (FIG. 5).

2-2: Observation of Changes in Nanoplasmonic Phenomenon

Changes in the nanoplasmonic phenomenon of the three samples of Example 2-1 were observed. The nanoplasmonic phenomenon is an optical phenomenon occurring in nanometer-sized gold nanoparticles. According to this phenomenon, genes present on the surface of metal nanoparticles resonate in response to incident light and absorb light at a particular wavelength to produce a color. The particular wavelength may vary depending on the size of the metal nanoparticles to produce different colors of light. When the metal nanoparticles are close to each other, the nanoplasmonic phenomenon is affected, and as a result, the particular wavelength varies.

Since the gold nanoparticles in Samples 1 and 2 were not bound to one another, the distances between the gold nanoparticles were maintained constant and the gold nanoparticles are uniformly dispersed. In contrast, since the gold nanoparticles in Sample 3 were complementarily bound to each other, the distances between the gold nanoparticles were close to one another, and as a result, a shift in the wavelength of absorbed light was observed. These results were confirmed by analyzing the absorption regions of the three samples using a spectrometer.

Figure 6:
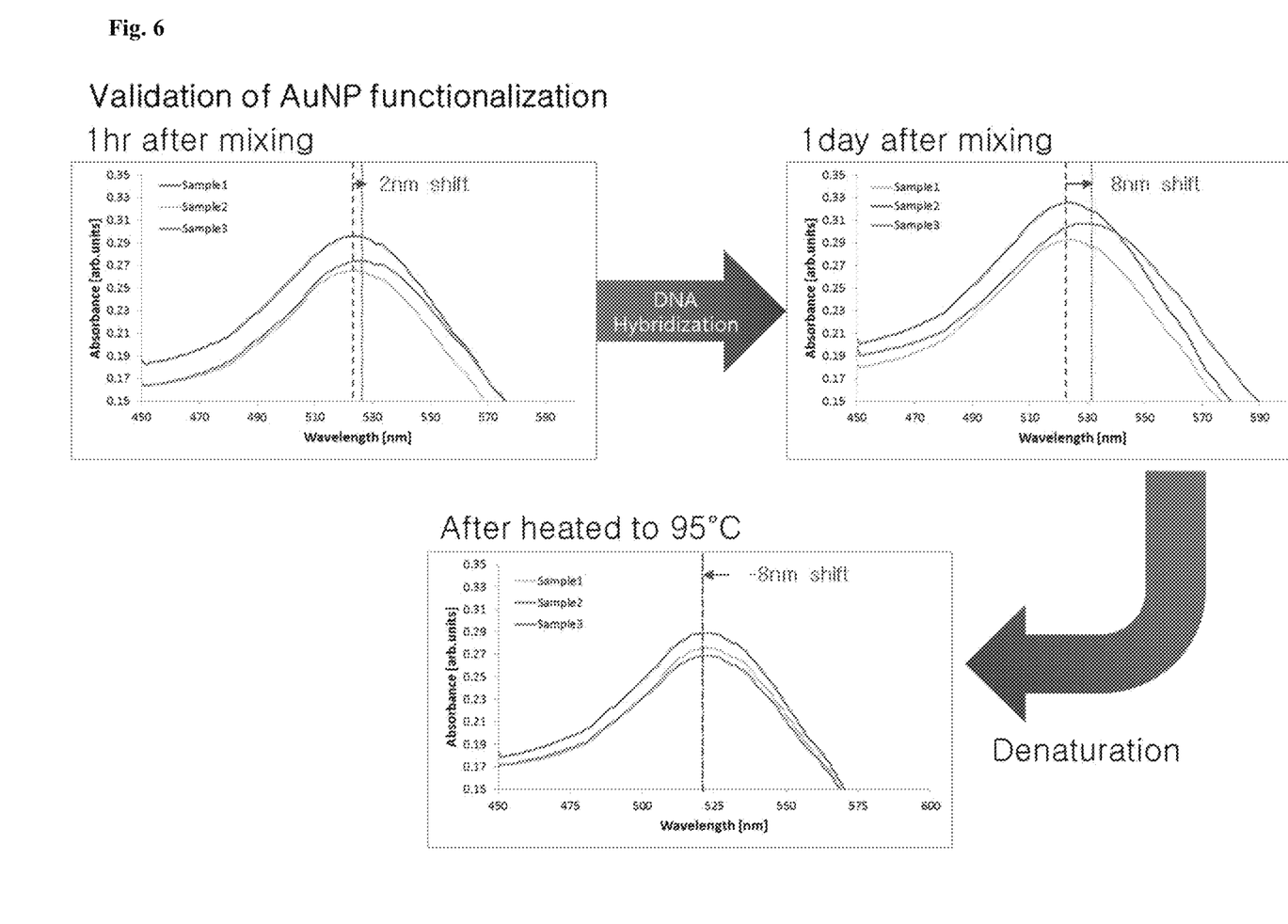
FIG. 6 shows changes in nanoplasmonic phenomenon by the surface treatment of gold nanoparticles in Example 2-2.

The absorption regions of Samples 1 and 2 did not vary 1 h and 1 day after mixing but the absorption region of Sample 3 was shifted by 2 nm 1 h after mixing and by 8 nm 1 day after mixing (FIG. 6).

Denaturation was performed to confirm whether the wavelength shift was caused by complementary binding between the DNAs. The denaturation refers to a process to cleave the complementary bonds between the DNAs by exposure to 95° C. After denaturation, the absorption region of Sample 3 was confirmed to return to its initial value, demonstrating the presence of the probe DNAs attached to the surface of the gold nanoparticles (FIG. 6).

2-3: Confirmation of Effect of Exonuclease III on DNA Digestion

Exonuclease III was used to digest the complementary double-stranded DNAs one by one from the 3' ends of the DNAs until the non-complementary sensing DNAs were reached. The reaction ended when no complementary double strands were present. As a result of the reaction, the target capture DNAs were removed from the gold nanoparticles.

Figure 7:
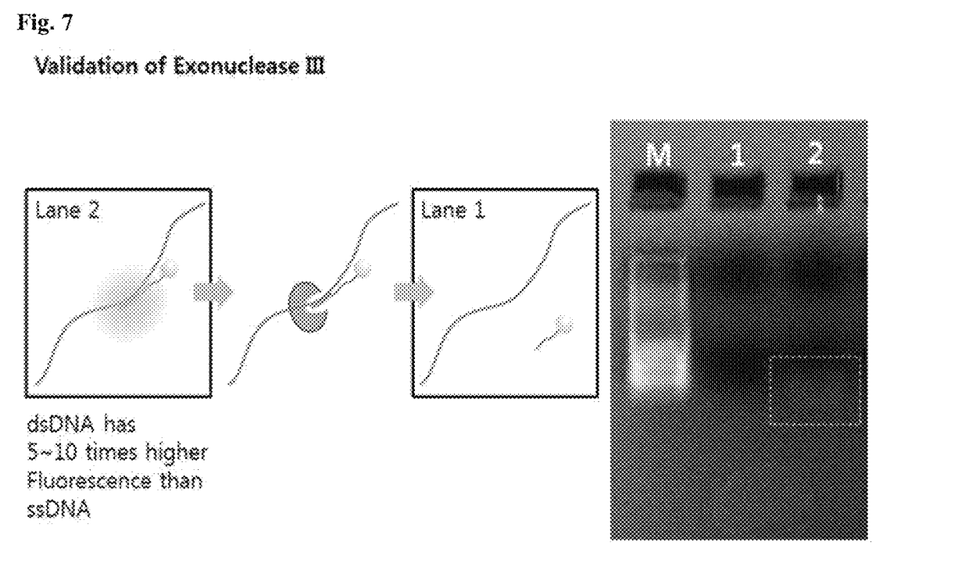
FIG. 7 shows an experiment for validating the effect of exonuclease III on DNA digestion in Example 2-3 and its results.

To confirm the digestion of the target capture DNAs, the double-stranded DNAs were left intact without the addition of exonuclease III in a sample in Lane 2 and exonuclease III was added to a sample in Lane 1. A sufficient time was allowed for the digestion of the double-stranded DNAs, as shown at the left of FIG. 7.

Thereafter, a fluorescent reagent emitting strong fluorescence only in the presence of double-stranded DNAs was added, followed by electrophoresis. As a result of fluorescence analysis, fluorescent bands were observed in the sample in Lane 2 due to the presence of double-stranded DNAs but no bands were observed in the sample in Lane 1 because the fluorescent reagent did not emit strong light by cleavage of the double-stranded DNAs, as shown at the right of FIG. 7.

These results demonstrate the ability of exonuclease III to digest the target capture DNAs.

2-4: Validation of Blocking Process

Figure 8:
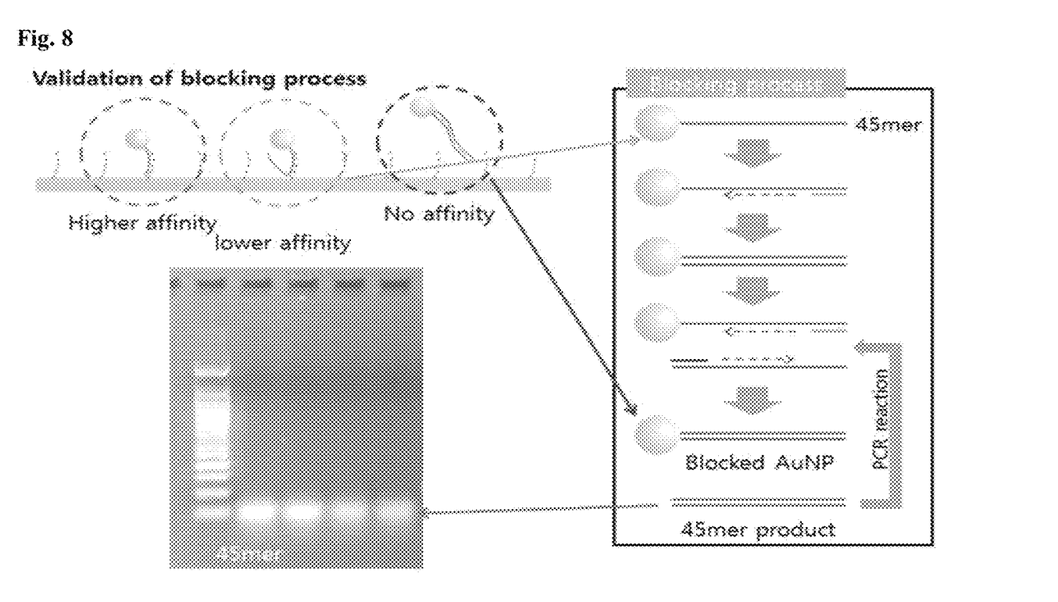
FIG. 8 shows a blocking process in Example 2-4 and its validation results.

To prevent the generation of false-positive signals from the probe-gold nanoparticles from which the target capture DNAs remain uncleaved by exonuclease III (shown at the top in the right box "Blocking process" of FIG. 8), the probe DNAs attached to the gold nanoparticles were made double-stranded to block them from binding to the surface.

Primers complementarily binding to the target capture DNAs (the second step in the right box "Blocking process" of FIG. 8) cannot bind to the probe DNAs of the probe-gold nanoparticles cleaved by exonuclease III but bind to the probe DNAs unaffected by exonuclease III.

Then, the primers were extended by PCR to form complementary double strands with the probe DNAs. The resulting double-stranded probe DNAs cannot complementarily bind to the DNAs immobilized on the sensor surface (the rightmost at the top left of FIG. 8).

To validate this blocking process, an investigation was made as to whether the addition of further primers (represented in red in the right box "Blocking process" of FIG. 8) continuously amplified the probe DNAs. The probe DNAs were 45-mer in length and their continuous amplification was observed by staining with a fluorescent reagent and subsequent electrophoresis. The continuous amplification indicates that the first initial reaction took place readily, demonstrating that the blocking process was successful. As shown at the bottom left of FIG. 8, PCR products corresponding to 45-mer were well detected, revealing that the blocking process was successful.

Although the particulars of the present disclosure have been described in detail, it will be obvious to those skilled in the art that such particulars are merely preferred embodiments and are not intended to limit the scope of the present invention. Therefore, the true scope of the present invention is defined by the appended claims and their equivalents.

What is claimed is:

1. A gene detection method comprising: (a) attaching a controlled number of probe DNAs for target gene detection to the surface of gold nanoparticles to form probe-gold nanoparticles, wherein each of the probe DNAs comprise a target capture DNA and a sensing DNA; (b) mixing the probe-gold nanoparticles in a sample such that the target capture DNA is hybridized with a single strand target gene, wherein the target capture DNA complementarily bound to the target gene comprises an exposed 3' end; (c) degrading the exposed 3' ends of the target capture DNAs complementarily bound to the target gene by a nuclease to remove from the probe DNA the target capture DNA complementarily bound to the target gene, thereby forming a product of the probe DNA comprising the sensing DNA; (d) allowing the target gene to return to its single strand; (e) repeating (b) to (d) to amplify the number of the product;

(f) synthesizing complementary blocking DNAs along probe DNAs of unreacted gold nanoparticles using a DNA polymerase, DNA strands as primers complementarily binding to target capture DNAs of the probe DNAs of the unreacted gold nanoparticles, and dNTPs, whereby the probe DNAs of the unreacted gold nanoparticles become double-stranded; and (g) allowing the sensing DNA of the product to complementarily bind to a probe linker DNA immobilized on a surface of a sensor to generate detection signals, wherein the detection signals are indicative of the target gene.

2. The method according to claim 1, wherein the sensor is one designed for surface measurement.

3. The method according to claim 1, wherein step (a) further comprises using short DNAs or surface treating materials whose length is smaller than the probe DNAs as spacers to prevent the probe DNAs from adhering to the entire surface of the gold nanoparticles and to allow only a predetermined number of the probe DNAs to be attached to the surface of the gold nanoparticles.

4. The method according to claim 1, wherein the number of the product is amplified from one target gene to achieve a signal amplification effect.

* * * * *